United States Patent [19]

Hester, Jr.

[11] 4,000,151
[45] Dec. 28, 1976

[54] TRIAZOLYL BENZOPHENONE COMPOUNDS

[75] Inventor: Jackson B. Hester, Jr., Galesburg, Mich.

[73] Assignee: The Upjohn Company, Kalamazoo, Mich.

[22] Filed: Sept. 12, 1975

[21] Appl. No.: 612,767

Related U.S. Application Data

[60] Continuation of Ser. No. 505,022, Sept. 11, 1974, abandoned, which is a continuation-in-part of Ser. No. 386,089, Aug. 6, 1973, abandoned, which is a division of Ser. No. 252,504, May 11, 1972, Pat. No. 3,812,140, which is a division of Ser. No. 114,049, Feb. 9, 1971, Pat. No. 3,709,898.

[52] U.S. Cl. ............... 260/308 R; 260/283 R; 260/288 R; 260/288 CF
[51] Int. Cl.² .......................... C07D 249/08
[58] Field of Search ............... 260/308 R

[56] References Cited

UNITED STATES PATENTS 3,709,898  1/1973  Hester .................. 260/308 R

OTHER PUBLICATIONS

Derieg et al., J. Het. Chem., vol. 8, pp. 181–182 (1971).

*Primary Examiner*—Alton D. Rollins
*Attorney, Agent, or Firm*—Hans L. Berneis

[57] ABSTRACT

Intermediates of the formula IV:

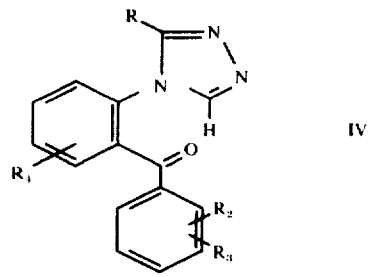

wherein R is selected from the group consisting of hydrogen and alkyl of 1 to 3 carbon atoms, inclusive; and wherein $R_2$, $R_3$, and $R_4$ are selected from the group consisting of hydrogen, fluoro, chloro, bromo, nitro, and trifluoromethyl are produced by a multistep synthesis. The final compounds are tranquilizers and sedatives and can be used in mammals, including man, and in birds.

3 Claims, No Drawings

TRIAZOLYL BENZOPHENONE COMPOUNDS

CROSS REFERENCES TO RELATED APPLICATIONS

This application is a continuation of application Ser. No. 505,022, filed Sept. 11, 1974, now abandoned which is a continuation in part of application Ser. No. 386,089, filed Aug. 6, 1973, now abandoned which is a divisional application of application Ser. No. 252,504, filed May 11, 1972, now U.S. Pat. 3,812,140 which is a division of application Ser. No. 114,049, filed Feb. 9, 1971, now U.S. Pat. No. 3,709,898

BACKGROUND OF THE INVENTION

Field of the Invention

This invention is directed to new organic compounds and is particularly concerned with a process for 2-(4H-1,2,4-triazol-4-yl)benzophenones.

The novel compounds and the process of production therefore can be illustratively represented as follows:

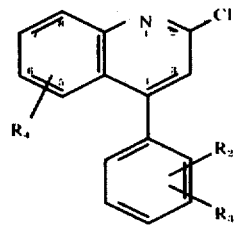

I

II

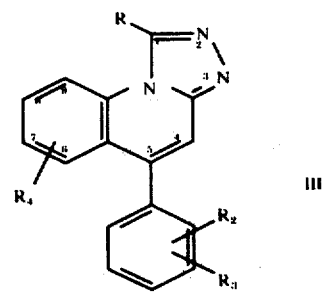

III

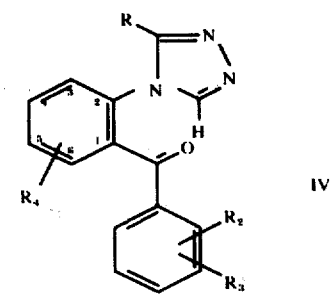

IV

The more desirable compounds in this invention are those of the formula:

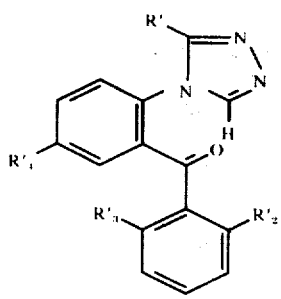

IVA wherein R' is hydrogen or methyl; wherein R'$_2$ is hydrogen, chloro, or fluoro; wherein R'$_3$ is hydrogen, or fluoro if R'$_2$ is fluoro; and wherein R'$_4$ is hydrogen, fluoro, chloro, or trifluoromethyl.

The most desirable products are of the formula:

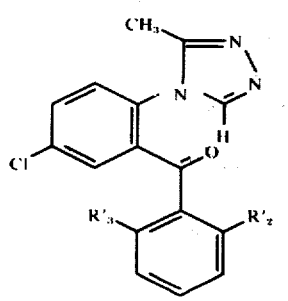

IVB wherein R'$_2$ is hydrogen, chloro, or fluoro; and wherein R'$_3$ is hydrogen, or fluoro if R$_2$ is fluoro.

The products of formula IV are useful per se as tranquilizers but their principal use is as intermediates for compounds of formula VII which are extremely potent tranquilizers. The compounds of formula VII are obtained from those of formula IV by the following scheme:

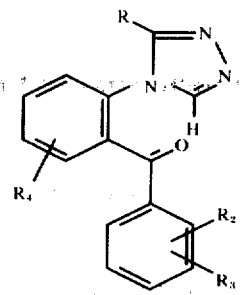

IV

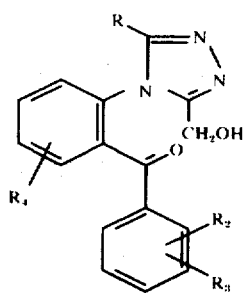

V

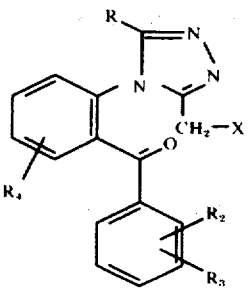

VI

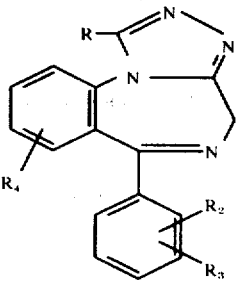

VII

The process of this invention comprises:
1. Refluxing a 2-chloro-4-phenylquinoline (I) with hydrazine hydrate to give a 2-hydrazino-4-phenylquinoline (II);
2. refluxing the 2-hydrazino-4-phenylquinoline (II) with a trialkyl orthoacylate e.g. with triethyl orthoformate, triethylorthoacetate, triethyl orthopropionate or trimethyl orthobutyrate, in an inert organic solvent, to give the corresponding 1-substituted-5-phenyl-s-triazolo-[4,3-a]quinoline (III);

3. treating III with an oxidizing agent or system such as ruthenium dioxide and sodium periodate or ozone in an inert solvent at low temperature to give a mixture containing mainly a 2-(3-substituted-4H-1,2,4-triazol-4-yl)-benzophenone (IV) and a 4-(2-benzoylphenyl)-5-substituted-4H-1,2,4-triazolo-3-carboxaldehyde;

The synthetic steps to produce from intermediates of formula IV the final products, comprises:

4. treating (IV) with formaldehyde to obtain a 2-[3-(hydroxymethyl)-5-substituted-4-H-1,2,4-triazol-4-yl]benzophenone (V).

5. converting alcohol (V) to a halide with a halogenating agent such as phosphorus tribromide, phosphorus oxychloride, phosphorus triiodide, or thionyl chloride to obtain the corresponding 2-[3-(halomethyl)-5-substituted-4H-1,2,4-triazol-4-yl]benzophenone (VI); and 6. treating (VI) with ammonia to give the corresponding 1-substituted-6-phenyl-4H-s-triazolo[4,3-a][1,4]benzodiazepine VII.

DESCRIPTION OF THE PREFERRED EMBODIMENT

Lower alkyl groups of 1 to 3 carbon atoms, inclusive, are exemplified by methyl, ethyl, propyl, and isopropyl.

The compounds of the formulae VII including acid addition salts thereof have sedative, tranquilizing, and muscle relaxant effects in mammals, including man and in birds.

The acid addition salts of compounds of formula VII contemplated in this invention, are the hydrochlorides, hydrobromides, hydriodes, sulfates, phosphates, cyclohexanesulfamates methanesulfonates and the like, prepared by reacting a compound of formula VII with an excess of the selected pharmacologically acceptable acid.

Sedative effects of 8-chloro-1-methyl-6-phenyl-4H-s-triazolo[4,3-a][1,4]benzodiazepine(a final product conforming to formula VII) are shown by the following tests in mice:

Chimney test: [Med. Exp. 4, 145 (1961)]: The effective intraperitoneal dosage for 50% of the mice ($ED_{50}$) is 0.09 mg./kg.; the oral $ED_{50}$ is 0.6 mg./kg. The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of the test compound at which 50% of the mice remain in the dish. The $ED_{50}$ (intraperitoneal administration) in this test is 0.15 mg./kg.; the oral $ED_{50}$ is 0.045 mg./kg.

Pedestal test: The untreated mouse leaves the pedestal in less than a minute to climb back to the floor of the standard mouse box. Tranquilized mice will stay on the pedestal for more than 1 minute. The $ED_{50}$ (oral administration) is 0.9 mg./kg.

Nicotine antagonism test: Mice in a group of 6 are injected with the test compound (8-chloro-1-methyl-6-phenyl-4H-s-triazolo[4,3-a][1,4]benzodiazepine). Thirty minutes later the mice, including control (untreated) mice are injected with nicotine salicylate (2 mg./kg.). The control mice show overstimulation, i.e., (1) running convulsions followed by (2) tonic extensor fits, followed by (3) death. An intraperitoneal dosage of 0.1 mg./kg. of the test compound protected 50% of the mice against (2) and (3) ($ED_{50}$); the oral $ED_{50}$ is 0.04 mg./kg.

Antagonism to strychnine (as sulfate): The effective dosage ($ED_{50}$) of 8-chloro-1-methyl-6-phenyl-4H-s-triazolo[4,3-a][1,4]benzodiazepine is 1 mg./kg. orally in mice. The test consists of orally administering into groups of 6 mice the test compound, 8-chloro-1-methyl-6-phenyl-4H-s-triazolo-[4,3-a][1,4]-benzodiazepine, and 30 minutes later 3 mg./kg. strychnine sulfate intraperitoneally. The survivors after 4 hours reflect the activity of the compound as a muscle relaxant and antispasmodic. A dosage of 3 mg./kg. of strychnine sulfate is routinely fatal to all the control mice.

The following compounds have an (by intraperitoneal injection) $ED_{50}$ as shown in Table I below:

TABLE I

| COMPOUND | $ED_{50}$ (in mg./kg.) | | | |
|---|---|---|---|---|
| | Ch | C | P | Ni |
| 8-chloro-1-methyl-6-(2,6-difluorophenyl)-4H-s-triazolo-[4,3-a][1,4]benzodiazepine | 0.009 | 0.016 | 0.020 | 0.018 |
| 8-chloro-1-ethyl-6-phenyl-4H-s-triazolo[4,3-a][1,4]-benzodiazepine | 0.8 | 0.9 | 0.9 | 0.2 |
| 8-chloro-6-phenyl-4H-s-triazolo[4,3-a][1,4]-benzodiazepine | 0.25 | 0.4 | 0.7 | 0.08 |
| 8-trifluoromethyl-1-methyl-6-phenyl-4H-s-triazolo[4,3-a]-[1,4]benzodiazepine | 0.16 | 0.16 | 0.22 | 0.08 |
| 8-chloro-1-methyl-6-(o-chlorophenyl)-4H-s-triazolo-[4,3-a][1,4]benzodiazepine | 0.05 | 0.028 | 0.045 | 0.008 |
| 8-chloro-1-methyl-6-(o-fluorophenyl)-4H-s-triazolo-[4,3-a][1,4]benzodiazepine | 0.056 | 0.016 | 0.028 | 0.009 |

Ch = chimney test
D = dish test
P = pedestal test
Ni = nicotine antagonism (3) test The intermediates of formulae IV are also active tranquilizers and sedatives, but of lesser activity, as can be seen from Table II:

TABLE II

| COMPOUND | $ED_{50}$ (in mg./kg.) | | | |
|---|---|---|---|---|
| | Ch | D | P | Ni |
| 5-chloro-2-(3-methyl-4H-1,2,4-triazole-4-yl)benzophenone | 28 | 23 | 20 | 20 |

The pharmaceutical forms contemplated by this invention include pharmaceutical compositions of formula VII suited for oral, parenteral and rectal use, e.g., tablets powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Water or oil, e.g., coconut oil, sesame oil, safflower oil, cottonseed oil, peanut oil may be used for preparing solutions or suspensions of the active drug.

Sweetening, coloring, and flavoring agents may be added.

For mammals and birds, food premixes, with starch, oatmeal, dried fishmeat, fishmeal, flour and the like can be prepared.

As tranquilizers, the compounds of formula I can be used in dosages of 0.01–2.0 mg./kg. in oral or injectable preparations as described above, to alleviate tension and anxiety in mammals, or birds, such as e.g., occurs when animals are in travel.

The starting materials of formula I of this invention, substituted and unsubstituted 2-chloro-4-phenylquinolines, are partially known in the art e.g., G. A. Reynolds and C. R. Hauser, J. Am. Chem. Soc. 72, 1852 (1950) or are prepared according to the methods shown in the preparations.

In carrying out the process of the present invention, a 2-chloro-4-phenylquinoline I is heated with hydrazine hydrate. In the preferred embodiment of this invention, the reaction is carried out at the reflux temperature of the mixture; however, temperatures between 25° and 118° C. with a reaction time of 1 to 18 hours are operative. A solvent, such as lower alkanol, e.g., methanol, ethanol, 1- and 2-propanol can be used but is not necessary. In the preferred embodiment of the invention, one hour reflux under nitrogen is sufficient. At the termination of the reaction, the mixture is concentrated, poured into water and the insoluble product collected on a filter. Purification is carried out by conventional means such as extraction, chromatography or more commonly recrystallization to obtain the corresponding 2-hydrazino-4-phenylquinoline II.

Compound II is converted to the corresponding 1-substituted-5-phenyl-s-triazolo[4,3-a]quinoline (III) by heating with a lower alkyl ester of an ortho carboxylic acid e.g. trimethyl or triethyl orthoacetate. Temperatures between 80°–170° C. are operative in this reaction. Solvents such as heptane, octane, methylcylohexane, benzene, toluene, xylene (o, m, or p) can be used but are not necessary. In the preferred embodiment of this invention, the reaction is carried out in a nitrogen atmosphere with a higher boiling solvent e.g. xylene, at the reflux temperature of the reaction mixture. Lower alkanols, produced during the reaction by decomposition of the ortho ester, can be removed by distillation. The product III is recovered and purified by conventional procedures e.g. concentration of the reaction mixture to dryness, extraction, chromatography and/or recrystallization.

Oxidation of compound III, depending on the oxidizing agent and reaction conditions used, produces 2-(3-substituted-4H-1,2,4-triazol-4-yl)benzophenone. The oxidation can be carried out with sodium periodate using potassium permanganate or ruthenium dioxide as catalysts or with ozone and the like. With ozone, also 1-substituted-5-phenyl-s-triazolo[4,3-a]quinolin-4(5H)-one was obtained. The oxidation with ruthenium dioxide and sodium periodate is performed between 0° and 30° C. for a period of 2 to 24 hours. The sodium periodate is used in excess of 5–100 times by weight compared to the weight of ruthenium dioxide. Mixtures of water and acetone are used as solvents. The reaction mixture can be filtered or first concentrated and then filtered, and the pure products can be obtained by conventional means e.g. extraction, chromatography, recrystallization, combinations of these methods and the like. The reacion can also be terminated by the addition of sodium iodide and sodium thiosulfate. This method of terminating the reaction is particularly useful, if an organic reagent is used as oxidant. In the ozone oxidation procedure, temperatures of 0°–30° C. are used during 12 to 24 hours and a solvent or a solvent system of inert organic solvents e.g. methanol, ethanol, methylene chloride, chloroform or a combination thereof and the like.

The conversion of intermediates of compounds of formula IV to the final compounds of formula VII is described in detail in U.S. Pat. No. 3,709,898.

The following examples are illustrative of the processes and products of the present invention, but are not to be construed as limiting.

The preparation of starting compounds I follows the following scheme:

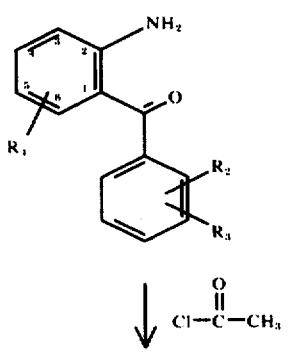

A

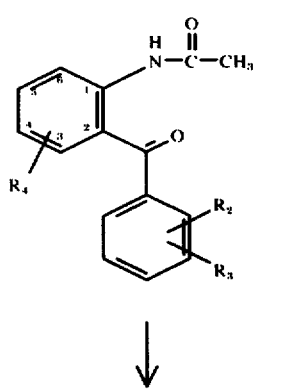

B

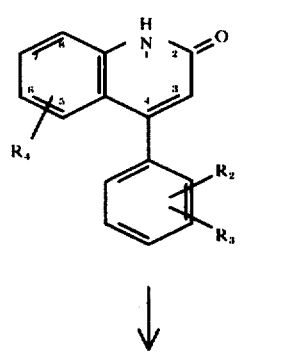

C

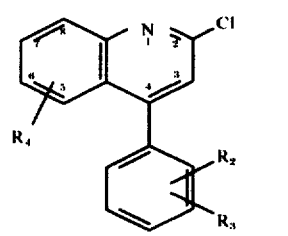

I wherein $R_2$, $R_3$, and $R_4$ are defined as herein before.

Preparation 1—2'-Benzoyl-4'-chloroacetanilide

Acetyl chloride (81.3 g., 1.037 mole) was added to a stirred solution of 2-amino-5-chlorobenzophenone (200.0 g., 0.864 mole) and pyridine (68.4 g., 0.864 mole) in dry ether (4 l.); the mixture was kept at ambient temperature for 2 hours and treated with 500 ml. of water. The layers were separated and the ether layer was dried over anhydrous sodium sulfate and concentrated. Crystallization of the residue from ethyl acetate-Skellysolve B hexanes gave: 124.0 g. of 2'-benzoyl-4'-chloroacetanilide of melting point 114°–115° C. Two more crops of 2'-benzoyl-4'-chloroacetanilide also were obtained: 67.8 g. of melting point 113.5°–114.5° C. and 33.0 g. of melting point 113°–114° C.

Preparation 2—6-Chloro-4-phenyl-2(1H)-quinolone

The procedure (reaction of 2'-benzoyl-5'-chloroacetanilide with sodium hydroxide) of A. E. Drukker and C. I. Judd, J., Heterocyclic Chem. 3, 359 (1966) was used for this preparation. The yield was 77%. Two other preparations have been described: S. C. Bell, T. S. Sulkowski, C. Gochman and S. J. Childress, J. Org. Chem. 27, 562 (1962); G. A. Reynolds and C. R. Hauser, J. Amer. Chem. Soc. 72, 1852 (1950).

Preparation 3—2, 6-Dichloro-4-phenylquinoline

The procedure of A. E. Drukker and C. I. Judd, J. Heterocyclic Chem. 3, 359 (1966) was used for this preparation. The yield was 62%.

Using in preparation 1, 2-amino-2', 5-dichlorobenzophenone instead of 2-amino-5-chlorobenzophenone provides 2'-(2-chlorobenzoyl)-4'-chloroacetanilide of melting point 108°–110° C.

In similar manner using other benzophenones such as described by Fryer et al J. Org. Chem. 30, 521 (1965); Saucy et al. Helv. Chim. Acta 45, 2226 (1962); Sternbach et al. J. Org. Chem. 26, 4488 (1961) and 27, 3781 (1962) and others, allows the preparation of:

2'-(2-chlorobenzoyl)acetanilide;
2'-benzoyl-4'-nitroacetanilide;
2'-benzoyl-4'-fluoroacetanilide;
2'-benzoyl-4'-(trifluoromethyl)acetanilide;
2'-benzoyl-4'-bromoacetanilide;
2'-(2-chlorobenzoyl)-4'-nitroacetanilide;
2'-(2-chlorobenzoyl)-4'-fluoroacetanilide;
2'-(2-chlorobenzoyl)-4'-(trifluoromethyl)acetanilide;
2'-(2-chlorobenzoyl)-4'-bromoacetanilide;
2'-(2-chlorobenzoyl)acetanilide;
2'-(2,6-difluorobenzoyl)-4'-chloroacetanilide;
2'-(4-fluorobenzoyl)-4'-chloroacetanilide;
2'-(2-fluorobenzoyl)-4'-chloroacetanilide;
2'-benzoylacetanilide;
and the like.

These compounds can be cyclized and reacted with phosphorus oxychloride like in preparations 2 and 3, to give starting compounds of formula 1, such as:

2,6-dichloro-4-(o-chlorophenyl)quinoline;
2,6-dichloro-4-(p-fluorophenyl)quinoline;
2-chloro-6-nitro-4-phenylquinoline;
2-chloro-6-fluoro-4-phenylquinoline;
2-chloro-6-(trifluoromethyl)-4-phenylquinoline;
2-chloro-6-bromo-4-phenylquinoline;
2-chloro-4-(2,6-difluorophenyl)quinoline;
2,6-dichloro-4-(2,6-difluorophenyl)quinoline;
2-chloro-6-fluoro-4-(o-chlorophenyl)quinoline;
2-chloro-6-nitro-4-(o-chlorophenyl)quinoline;
2-chloro-6-fluoro-4-(o-fluorophenyl)quinoline;
2-chloro-6-bromo-4-(o-chlorophenyl)quinoline;
2-chloro-6-(trifluoromethyl)-4-(o-chlorophenyl)quinoline;
2-chloro-4-(o-chlorophenyl)quinoline;
2-chloro-4-phenylquinoline;
and the like.

EXAMPLE 1

6-Chloro-2-hydrazino-4-phenylquinoline

A stirred mixture of 2,6-dichloro-4-phenylquinoline (2.7 g., 0.01 mole) and hydrazine hydrate (6.8 g.) is refluxed under nitrogen for 1 hour and concentrated in vacuo. The residue is suspended in warm water, and the solid is collected by filtration, dried and recrystallized from ethyl acetate-Skellysolve B hexanes to give 1.81 g. (67% yield) of 6-chloro-2-hydrazino-4-phenylquinoline of melting point 156.5°–157° C.

Anal. Calcd. for $C_{15}H_{12}ClN_3$: C, 66.79; H, 4.49; Cl, 13.15; N, 15.58. Found: C, 67.15; H, 4.65; Cl, 13.19; N, 15.32.

EXAMPLE 2

7-Chloro-1-methyl-5-phenyl-s-triazolo[4,3-a]-quinoline

A stirred mixture of 6-chloro-2-hydrazino-4-phenylquinoline (1.4 g., 0.0052 mole), triethyl orthoacetate (0.925 g., 0.0057 mole) and xylene (100 ml.) is refluxed, under nitrogen, for 2 hours 40 minutes. During this period the ethanol formed in the reaction is removed by distillation through a short, glass helizpacked column. The mixture is concentrated to dryness in vacuo and the residue is crystallized from methanol-ethyl acetate to give: 1.02 g. of 7-chloro-1-methyl-5-phenyl-s-triazolo-[4,3-a]quinoline of melting point 253.5°–255° C. and 0.26 g. of melting point 253.5°–255° C. (83.9% yield). The analytical sample is crystallized from methylene chloride:methanol and has a melting point 252.5°–253.5° C.

Ana. Anal. for $C_{17}H_{12}ClN_3$: C, 69.50; H, 4.12; Cl, 12.07; N, 14.49. Found: C, 69.39; H, 4.02; Cl, 12.10; N, 14.49.

EXAMPLE 3

5-Chloro-2-(3-methyl-4H-1,2,4triazol-4-yl)benzophenone (Oxidation of 7-chloro-1-methyl-5-phenyl-s-triazolo[4,3-a]quinoline)

A stirred suspension of 7-chloro-1-methyl-5-phenyl-s-triazolo[4,3-a]quinoline (2.94 g., 0.01 mole) in acetone (110 ml.) is cooled in an ice-bath and treated slowly with a solution prepared by adding sodium periodate (2 g.) to a stirred suspension of ruthenium dioxide (200 mg.) in water (35 ml.). The mixture becomes dark. Additional sodium periodate (8 g.) is added during the next 15 minutes. The ice bath is removed and the mixture is stirred for 45 minutes. Additional sodium periodate (4 g.) is added and the mixture is stirred at ambient temperature for 18 hours and filtered. The solid is washed with acetone and the combined filtrate is concentrated in vacuo. The residue is suspended in water and extracted with methylene chloride. The extract is dried over anhydrous potassium carbonate and concentrated. The residue is chromatographed on silica gel (100 g.) with 10% methanol 90% ethyl acetate; 50 ml. fractions are collected. The product is eluted in fractions 10–20 and is crystallized from ethyl acetate to give: 0.405 g. of melting point 168°–169.5° C. and 0.291 g. of melting point 167.5°–169° (23.4% yield) of 5-chloro-2-(3-methyl-4H-1,2,4-triazol-4-yl)benzophenone. The analytical sample has a melting point of 168° C.

Anal. calcd. for $C_{16}H_{12}ClN_3O$: C, 64.54; H, 4.06; Cl, 11.91; N, 14.11. Found: C, 64.56; H, 4.35; Cl, 11.97; 11.93; N, 14.29.

EXAMPLE 4

Oxidation of 7-chloro-1-methyl-5-phenyl-s-triazolo[4,3-a]quinoline

A stirred suspension of 7-chloro-1-methyl-5-phenyl-s-triazolo[4,3-a]quinoline (2.94 g., 0.01 mole) and acetone (200 ml.) is cooled in an ice bath and treated, dropwise, during 15 minutes with a solution prepared from ruthenium dioxide (200 mg.), sodium periodate (4 g.) and water (35 ml.). A slight exothermic reaction is noted and the mixture becomes dark. After 10 minutes 29 ml. of a solution of sodium periodate (12 g.) in water (70 ml.) is added during 10 minutes. This mixture is stirred for 2 hours and then the remaining sodium periodate solution (41 ml.) is added during the next 3 hours. The mixture is concentrated in vacuo to remove acetone. The resulting aqueous mixture is extracted with methylene chloride. The extract is washed with water, dried over anhydrous magnesium sulfate, and concentrated. The residue is chromatographed on silica gel (150 g.) with 2% methanol-98% chloroform; 60 ml. fractions are collected. Recovered starting material is eluted in fractions 11–14 and crystallized from methanolmethylene chloride to give 0.069 g. of melting point 251.5–253.5° C. A mixture of the two products is eluted in fractions 15–39. Crystallization of this mixture from ethyl acetate gives 618 mg. (20.8%) of 5-chloro-2-(3-methyl-4H-1,2,4-triazol-4-yl)benzophenone of melting point 165.5°–168°. Crystallization of the mother liquor from methanol gives 0.126 g., melting point 108°–112°and 0.588 g. of melting point 101.5°–105.5° (decomposition) (19.9% yield) of a methanol solvate of 4-(2-benzoyl-4-chlorophenyl)-5-methyl-4H-1,2,4-triazole-3-carboxaldehyde. The analytical sample has a melting point 100°–101.5° C.

Anal. calcd. for $C_{17}H_{12}ClN_3O_2$: C, 62.68; H, 3.71; Cl, 10.89; N, 12.90. Found: C, 59.37; H, 4.89; Cl, 9.75; N, 11.30.

MeOH, 9.34%; $H_2O$, 0.40%. Corrected for MeOH and $H_2O$: C, 61.90; H, 4.06; Cl, 10.80; N, 12.52.

Heating the solvate in a desiccator at 70° C. at 15 mm. Hg for 72 hours gives pure 4-(2-benzoyl-4-chlorophenyl)-5-methyl-4H-1,2,4-triazole-3-carboxaldehyde.

EXAMPLE 5

Oxidation of 7-chloro-1-methyl-5-phenyl-s-triazolo[4,3-a]quinoline

A vigorous stream of ozone in oxygen is bubbled for 12 hours, into a stirred, ice-cold solution of 7-chloro-1-methyl-5-phenyl-s-triazolo[4,3-a]quinoline (31.1 g., 0.106 mole) in methanol (750 ml.) and methylene chloride (500 ml.0. The resulting mixture is filtered and the filtrate is added to an ice-cold solution of sodium iodide (47.5 g.) and acetic acid (63 ml.) in water (200 ml.). The solution is decolorized by the addition of sodium thiosulfate and concentrated in vacuo. The residue is mixed with water and extracted with methylene chloride. The extract is washed ($H_2O$), dried over anhydrous magnesium sulfate and concentrated. The residue is chromatographed on silica gel (1.5 kg.); 175 ml. fractions are collected. Fractions 1–128 are eluted with 1% methanol -99% chloroform and fractions 129–168 with 5% methanol-95% chloroform. The first compound is eluted in fractions 49–60 and crystallized from methanol-ethyl acetate to give: 0.769 g. of melting point 229.5°–231° (decomposition) and 0.535 g. of melting point 228° (decomposition) of 7-chloro-1-methyl-5-phenyl-s-triazolo[4,3-a]quinolin-4(5H)-one. The analytical sample has a melting point 232°–233° C.

Anal. calcd. for $C_{17}H_{12}ClN_3O$: C, 65.92; H, 3.91; Cl, 11.44; H, 13.57. Found: C, 65.46; H, 3.72; Cl, 11.48; N, 13.59.

Recovered starting material is eluted in fractions 66–78 and crystallized from methylene chloride-methanol to give 0.737 g. of melting point 251°–253° C. A mixture of the two remaining products is eluted in fractions 73–168. Crystallization of this mixture from ethyl acetate gives: 10.8 g. of melting point 166.5°–167.5° C., 0.987 g. of melting point 166°–167° C. and 2.52 g. of melting point of 164°–165.5° C. (45.3% yield) of 5-chloro-2-(3-methyl-4H-1,2,4-triazol-4-yl)benzophenone. Crystallization of the mother liquor from methanol gives 5.62 g. of melting point 140°–141.5° C., 1.23 g. of melting point 100.5°–102.5° (decomposition) and 1.04 g. of melting point 105°–137° (20.8% yield) of 4-(2-benzoyl-4chlorophenyl)-5-methyl-4H-1,2,4-triazole-3-carboxaldehyde.

EXAMPLE 6

5-Chloro-2-[3-hydroxymethyl)-5-methyl-4H-1,2,4-triazol-4-yl]benzophenone

A stirred mixture of 5-chloro-2-(3-methyl-4H-1,2,3-triazolo-4-yl)benzophenone, (2.98 g., 0.01 mole) paraformaldehyde (3 g.) and xylene (100 ml.) is warmed under nitrogen in a bath maintained at 125° C. for 7 hours. The mixture is then concentrated in vacuo. The residue is chromatographed on silica gel (150 g.) with 3% methanol-97% chloroform. Fifty ml. fractions are collected. The product is eluted in fractions 20–44. The fractions are concentrated and the residue is crystallized from ethanol-ethyl acetate to give: 1.64 g. of melting point 138°–142° C.; 0.316 g. of melting point 138.5°–141° C,; 0.431 g. of melting point 139°–141° C. (72.8% yield) of 5-chloro-2-[3-(hydroxymethyl)-5-4H-1,2,4-triazol-4-yl]benzophenone. The analytical sample has a melting point of 138°–139° C.

Anal. calcd. for $C_{17}H_{14}ClN_3O_2$: C, 62.30; H, 4.30; Cl, 10.81; N, 12.82. Found: C, 62.23; H, 4.22; Cl, 10.82; N, 11.73.

EXAMPLE 7

5-Chloro-2-[3-(bromomethyl)-5-methyl-4H-1,2,4-triazol-4-yl]benzophenone

A solution of 5-chloro-2-[3-(hydroxymethyl)-5-methyl-4H-1,2,4-triazol-4-yl]benzophenone (328 mg., 0.001 mole) in dry, hydrocarbon-stabilized chloroform (5 ml.) is cooled in an ice bath and treated with phosphorus tribromide (0.1 ml.). The colorless solution is kept in the ice bath for 55 minutes, at ambient temperature (22–24° C.), for 5 hours. The resulting yellow solution is poured into a mixture of ice and dilute sodium bicarbonate. This mixture is extracted with chloroform. The extract is washed with brine, dried over anhydrous magnesium sulfate and concentrated. The residue is crystallized from methylene chloride-ethyl acetate to give: 0.285 g. of melting point 200°–240° (decomposition) and 0.030 g. of melting point 200°–220° C. (decomposition) of 5-chloro-2-[3-(bromomethyl)-5-methyl-4H-1,2,4-triazol-4-yl]benzophenone. The analytical sample has a melting point of 200°–240° C.

Anal. calcd. for $C_{17}H_{13}BrClN_3O$: C, 52.26; H, 3.35; Br, 20.46; Cl, 9.08; N, 10.76. Found: C, 52.13; 52.45; H, 3.77; 3.66; Br, 20.44; Cl, 9.20; N, 10.43.

EXAMPLE 8

5-Chloro-2-[3-(chloromethyl)-5-methyl-4H-1,2,4-triazol-4-yl]benzophenone

A solution of 5-chloro-2-[3-(hydroxymethyl)-5-methyl-4H-1,2,4-triazol-4-yl]benzophenone (328 mg., 0.001 mole) in thionyl chloride (2 ml.) is warmed during 40 minutes to a bath temperature of 78° C. and kept at 78°–83° C. for 1 hour 25 minutes. It is then cooled and poured into ice water. This mixture is neutralized with sodium bicarbonate and extracted with chloroform. The extract is washed with brine, dried over anhydrous magnesium sulfate and concentrated in vacuo. The residue is crystallized from ethyl acetate Skellysolve B hexanes to give: 0.240 g. of melting point 144.5°–147° C. and 0.045 g. of melting point 144.5°–146.5° C. of 5-chloro-2-[3-(chloromethyl)-5-methyl-4H-1,2,4-triazol-4-yl]benzophenone. The analytical sample has a melting point of 139°–140° C.

Anal. Calcd. for $C_{17}H_{13}Cl_2N_3O$: C, 58.96; H, 3.78; Cl, 20.48; N, 12.14. Found: C, 59.22; H, 3.80; Cl, 20.66; N, 11.91.

EXAMPLE 9

5-Chloro-2-[3-(iodomethyl)-5-methyl-4H-1,2,4-triazol-4-yl]benzophenone

5-Chloro-2-[3-(chloromethyl)-5-methyl-4H-1,2,4-triazol-4-yl]benzophenone (346 mg. 0.001 mole) is added to a stirred solution of sodium iodide (300 mg., 0.002 mole) in acetone, and the resulting mixture is stirred at ambient temperature for 6 hours 54 minutes and poured into ice water. This mixture is extracted with chloroform. The extract is washed with brine, dried and concentrated. The residue is crystallized from methylene chloride-ethyl acetate to give: 0.227 g. of melting point 185.5°–192° (decomposition) of 5-chloro-2-[3-(iodomethyl)-5-methyl-4H-1,2,4-triazol-4-yl]benzophenone. The analytical sample has a melting point of 185°–200° C. (decomposition).

Anal. calcd. for $C_{17}H_{13}ClIN_3O$: C, 46.65; H, 2.99; Cl, 8.10; I, 29.00; N, 9.60. Found: C, 46.78; H, 2.88; Cl, 8.59; I, 26.98; N, 9.23.

EXAMPLE 10

8-Chloro-1-methyl-6-phenyl-4H-s-triazolo[4,3-a][1,4]benzodiazepine

A stirred suspension of 5-chloro-2-[3-(bromomethyl)-5-methyl-4H-1,2,4-triazol-4-yl]benzophenone (391 mg., 0.001 mole) in tetrahydrofuran (15 ml.) is cooled in an ice bath and treated with a saturated solution of ammonia in methanol (12.5 ml.). The resulting solution is allowed to warm to ambient temperature and stand for 24 hours. It is then concentrated in vacuo. The residue is suspended in water, treated with a little sodium bicarbonate and extracted with methylene chloride. The extract is washed with brine, dried with anhydrous potassium carbonate and concentrated. The residue is crystallized from methylene chloride-ethyl acetate to give 0.229 g. of crude product of melting point 227°–228.5° C. Recrystallization of this material from ethyl acetate gives three crops of 8-chloro-1- methyl-6-phenyl-4H-s-triazolo[4,3-a][1,4]benzodiazepine: 0.142 g. of melting point 228°–229.5°, 0.053 g. of melting point 228.5°–229.5° C. and 0.021 g. of melting point 228°–229.5° C.

EXAMPLE 11

6-Chloro-4-(2,6-difluorophenyl)-2-hydrazinoquinoline

In the manner given in Example 1, 2,6-dichloro-4-(2,6-difluorophenyl)quinoline is reacted at reflux with hydrazine hydrate to give 6-chloro-4-(2,6-difluorophenyl)-2-hydrazinoquinoline.

EXAMPLE 12

7-Chloro-1-methyl-5-(2,6-difluorophenyl)-s-triazolo[4,3-a]quinoline

In the manner given in Example 2, 6-chloro-4-(2,6-difluorophenyl)-s-hydrazinoquinoline and triethyl orthoacetate are refluxed in xylene to give 7-chloro-1-methyl-5-(2,6-difluorophenyl)-s-triazolo[4,3-a]quinoline.

EXAMPLE 13

5-Chloro-2',6'-difluoro-2-(3-methyl-4H-1,2,4-triazol-4-yl)benzophenone

In the manner given in Example 3, 7-chloro-1-methyl-5-(2,6-difluorophenyl)-s-triazolo[4,3-a]quinoline is oxidized at low temperature with sodium periodate and ruthenium dioxide to give 5-chloro-2',6'-difluoro-2-(3-methyl-4H-1,2,4-triazol-4-yl)benzophenone.

EXAMPLE 14

5-Chloro-2',6'-difluoro-2-[3-(hydroxymethyl)-5-methyl-4H-1,2,4-triazol-4-yl]benzophenone In the manner given in Example 6, 5-chloro-2',6'-difluoro-2-(3-methyl-4H-1,2,4-triazol-4-yl)benzophenone is heated with paraformaldehyde at 125° C. to give 5-chloro-2',6'-difluoro-2-[3-(hydroxymethyl)-5-methyl-4H-1,2,4-triazol-4-yl]benzophenone.

EXAMPLE 15

5-Chloro-2',6'-difluoro-2-[3-(bromomethyl)-5-methyl-4H-1,2,4-triazol-4-yl]benzophenone In the manner given in Example 7, 5-chloro-2',6'-difluoro-2-[3-(hydroxymethyl)-5-methyl-4H-1,2,4-triazol-4-yl]benzophenone is treated with phosphorus tribromide to give 5-chloro-2',6'-difluoro-2-[3-(bromomethyl)-5-methyl-4H-1,2,4-triazol-4-yl]benzophenone.

EXAMPLE 16

8-Chloro-1-methyl-6-(2,6-difluorophenyl)-4H-s-triazolo[4,3-a][1,4]benzodiazepine

In the manner given in Example 10, 5-chloro-2',6'-difluoro-2-[3-(bromomethyl)-5-methyl-4H-1,2,4-triazol-4-yl]benzophenone is reacted with a saturated solution of ammonia in methanol to give 8-chloro-1-methyl-6-(2,6-difluorophenyl)-4H-s-triazolo[4,3-a][1,4]benzodiazepine of melting point 126°–127° C. (decomposition).

EXAMPLE 17

6-Chloro-4-(o-chlorophenyl)-2-hydrazinoquinoline

In the manner given in Example 1, 2,6-dichloro-4-(o-chlorophenyl)quinoline is reacted at reflux with hydrazine hydrate to give 6-chloro-4-(o-chlorophenyl)-2-hydrazinoquinoline.

EXAMPLE 18

7-Chloro-1-methyl-5-(o-chlorophenyl)-s-triazolo[4,3-a]quinoline

In the manner given in Example 2, 6-chloro-4-(o-chlorophenyl)-2-hydrazinoquinoline and triethyl orthoacetate are refluxed in xylene to give 7-chloro-1-methyl-5-(o-chlorophenyl)-s-triazolo[4,3-a]quinoline of melting point 257°–259° C.

EXAMPLE 19

2'5-Dichloro-2-(3-methyl-4H-1,2,4-triazol-4-yl)benzophenone.

In the manner given in Example 3, 7-chloro-1-methyl-5-(o-chlorophenyl)-s-triazolo[4,3-a]quinoline is oxidized at low temperature with sodium periodate and ruthenium dioxide to give 2',5-dichloro-2-(3-methyl-4H-1,2,4-triazol-4-yl)benzophenone of melting point 147.5°–148.5° C.

EXAMPLE 20

6-Nitro-4-(o-chlorophenyl)-2-hydrazinoquinoline

In the manner given in Example 1, 2-chloro-6-nitro-4-(o-chlorophenyl)quinoline is reacted at reflux with hydrazine hydrate to give 6-nitro-4-(o-chlorphenyl)-2-hydrazinoquinoline

EXAMPLE 21

7-Nitro-1-methyl-5-(o-chlorophenyl)-s-triazolo[4,3-a]quinoline

In the manner given in Example 2, 6-nitro-4-(o-chlorophenyl)-2-hydrazinoquinoline, and triethyl orthoacetate are refluxed in xylene to give 7-nitro-1-methyl-5-(o-chlorophenyl)-s-triazolo[4,3-a]quinoline.

EXAMPLE 22

2'-Chloro-5-nitro-2-(3-methyl-4H-1,2,4-triazol-4-yl)benzophenone

In the manner given in Example 3, 7-nitro-1-methyl-5-(o-chlorophenyl)-s-triazolo[4,3-a]quinoline is oxidized at low temperature with sodium periodate and ruthenium dioxide to give 2'-chloro-5-nitro-2-(3-methyl-4H-1,2,4-triazol-4-yl)benzophenone.

EXAMPLE 23

6-Fluoro-4-(o-chlorophenyl)-2-hydrazinoquinoline

In the manner given in Example 1, 2-chloro-6-fluoro-4-(o-chlorophenyl)quinoline is reacted at reflux with hydrazine hydrate to give 6-fluoro-4-(o-chlorophenyl)-2-hydrazinoquinoline.

EXAMPLE 24

7-Fluoro-1-methyl-5-(o-chlorophenyl)-s-triazolo[4,3-a]quinoline

In the manner given in Example 2, 6-fluoro-4-(o-chlorophenyl)-2-hydrazinoquinoline and triethyl orthoacetate are refluxed in xylene to give 7-fluoro-1-methyl-5-(o-chlorophenyl)-s-triazolo[4,3-a]quinoline.

EXAMPLE 25

5-Fluoro-2'-chloro-2-(3-methyl-4H-1,2,4-triazol-4-yl)benzophenone

In the manner given in Example 3, 7-fluoro-1-methyl-5-(o-chlorophenyl)-s-triazolo[4,3-a]quinoline is oxidized at low temperature with sodium periodate and ruthenium dioxide to give 5-fluoro-2'-chloro-2-(3-methyl-4H-1,2,4-triazol-4-yl)benzophenone.

EXAMPLE 26

6-(Trifluoromethyl)-4-(o-chlorophenyl)-2-hydrazinoquinoline

In the manner given in Example 1, 6-(trifluoromethyl)-2-chloro-4-(o-chlorophenyl)quinoline is reacted at reflux with hydrazine hydrate to give 6-(trifluoromethyl)-4-(o-chlorophenyl)-2-hydrazinoquinoline.

EXAMPLE 27

7-(Trifluoromethyl)-1-methyl-5-(o-chlorophenyl)-s-triazolo[4,3-a]quinoline

In the manner given in Example 2, 6-(trifluoromethyl)-4-(o-chlorophenyl)-2-hydrazinoquinoline and triethyl orthoacetate are refluxed in xylene to give 7-(trifluoromethyl)-1-methyl-5-(o-chlorophenyl)-s-triazolo[4,3-a]quinoline.

EXAMPLE 28

5-(Trifluoromethyl)-2'-chloro-2-(3-methyl-4H-1,2,4-triazol-4-yl)benzophenone

In the manner given in Example 3, 7-(trifluoromethyl)-5-(o-chlorophenyl)-s-triazolo[4,3-a]quinoline is oxidized at low temperature with sodium periodate and ruthenium dioxide to give 5-(trifluoromethyl)-2'-chloro-2-(3-methyl-4H-1,2,4-triazol-4-yl)benzophenone.

EXAMPLE 29

6-Nitro-4-phenyl-2-hydrazinoquinoline

In the manner given in Example 1, 2-chloro-6-nitro-4-phenylquinoline is reacted at reflux with hydrazine hydrate to give 6-nitro-4-phenyl-2-hydrazinoquinoline.

EXAMPLE 30

7-Nitro-1-methyl-5-phenyl-s-triazolo[4,3-a]quinoline

In the manner given in Example 2, 6-nitro-4-phenyl-2-hydrazinoquinoline and triethyl orthoacetate are refluxed in xylene to give 7-nitro-1-methyl-5-phenyl-s-triazolo[4,3-a]quinoline.

EXAMPLE 31

5-Nitro-2-(3-methyl-4H-1,2,4-triazol-4-yl)benzophenone

In the manner given in Example 3, 7-nitro-1-methyl-5-phenyl-s-triazolo[4,3-a]quinoline is oxidized at low temperature with sodium periodate and ruthenium dioxide to give 5-nitro-2-(3-methyl- 4H-1,2,4-triazol-4-yl)-benzophenone.

EXAMPLE 32

4-(o-Chlorophenyl)-2-hydrazinoquinoline

In the manner given in Example 1, 2-chloro-4-(o-chlorophenyl)quinoline is reacted at reflux with hydrazine hydrate to give 4-(o-chlorophenyl)-2-hydrazinoquinoline.

EXAMPLE 33

1-methyl-5-(o-chlorophenyl)-s-triazolo[4,3-a]quinoline

In the manner given in Example 2, 4-(o-chlorophenyl)-2-hydrazinoquinoline and triethyl orthoacetate are refluxed in xylene to give 1-methyl-5-(o-chlorophenyl)-s-triazolo[4,3-a]quinoline.

EXAMPLE 34

2'-Chloro-2-(3-methyl-4H-1,2,4-triazol-4-yl)benzophenone

In the manner given in Example 3, 1-methyl-5-(o-chlorophenyl)-s-triazolo[4,3-a]quinoline is oxidized at low temperature with sodium periodate and ruthenium dioxide to give 2'-chloro-2-(3-methyl-4H-1,2,4-triazol-4-yl)benzophenone.

EXAMPLE 35

6-Chloro-4-phenyl-2-hydrazinoquinoline

In the manner given in Example 1, 2,6-dichloro-4-phenylquinoline is reacted at reflux with hydrazine hydrate to give 6-chloro-4-phenyl-2-hydrazinoquinoline.

EXAMPLE 36

7-Chloro-5-phenyl-s-triazolo[4,3-a]quinoline

In the manner given in Example 2, 6-chloro-4-phenyl-2-hydrazinoquinoline and triethyl orthoformate are refluxed in xylene to give 7-chloro-5-phenyl-s-triazolo[4,3-a]quinoline of melting point 265°–266.5° C.

EXAMPLE 37

5-Chloro-2-(4H-1,2,4-triazol-4-yl)benzophenone

In the manner given in Example 3, 7-chloro-5-phenyl-s-triazolo[4,3-a]quinoline is oxidized at low temperature with sodium periodate and ruthenium dioxide to give 5-chloro-2-(4H-1,2,4-triazol-4-yl)benzophenone.

In the manner given in the preceding examples, other 2-(4H-1,2,4-triazol-4-yl)benzophenones of formula IV can be synthesized. Representative compounds thus obtained include:

2-(4H-1,2,4-triazol-4-yl)benzophenone;
2',5-dichloro-2-(4H-1,2,4-triazol-4-yl)benzophenone;
5-bromo-2-(3-methyl-4H-1,2,4-triazol-4-yl)benzophenone;
2'-chloro-5-bromo-2-(3-methyl-4H-1,2,4-triazol-4-yl)benzophenone;
2'-chloro-5-(trifluoromethyl)-2-(4H-1,2,4-triazol-4-yl)benzophenone;
2',6'-difluoro-2-(3-methyl-4H-1,2,4-triazol-4-yl)benzophenone;
4-chloro-2'-fluoro-2-(3-methyl-4H-1,2,4-triazol-4-yl)benzophenone;
3-nitro-3'-chloro-2-(3-methyl-4H-1,2,4-triazol-4-yl)benzophenone;
3-(trifluoromethyl-2'-fluoro-2-(3-methyl-4H-1,2,4-triazol-4-yl)benzophenone;
2'-fluoro-2-(3-ethyl-4H-1,2,4-triazol-4-yl)benzophenone;

3'-fluoro-2-(3-propyl-4H-1,2,4-triazol-4-yl)benzophenone;

5-chloro-2-(3-isopropyl-4H-1,2,4-triazol-4-yl)benzophenone;

4-nitro-2'-chloro-2-(3-ethyl-4H-1,2,4-triazol-4-yl)benzophenone;

6-bromo-2'-chloro-2-(3-ethyl-4H-1,2,4-triazol-4-yl)benzophenone;

2',5-dichloro-2-(3-propyl-4H-1,2,4-triazol-4-yl)benzophenone;

5-fluoro-2-(3-methyl-4H-1,2,4-triazol-4-yl)benzophenone;

5-(trifluoromethyl)-2-(3-methyl-4H-1,2,4-triazol-4-yl)benzophenone;

2-(3-methyl-4H-1,2,4-triazol-4-yl)benzophenone;

6-chloro-2',6'-difluoro-2-(3-methyl-4H-1,2,4-triazol-4-yl)benzophenone;

and the like.

I claim:

1. 5-Chloro-2-(3-methyl-4H-1,2,4-triazol-4-yl)benzophenone.

2. 2',5-Dichloro-2-(3-methyl-4H-1,2,4-triazol-4-yl)benzophenone.

3. 5-Chloro-2',6'-difluoro-2-(3-methyl-4H-1,2,4-triazol-4-yl)benzophenone.

* * * * *

UNITED STATES PATENT OFFICE
CERTIFICATE OF CORRECTION

Patent No. 4,000,151         Dated 28 December 1976

Inventor(s) Jackson B. Hester, Jr.

It is certified that error appears in the above-identified patent and that said Letters Patent are hereby corrected as shown below:

Column 11, line 35, "Ana. Anal." should read -- Anal. Calcd. --.
Column 11, line 36, "14.49" should read -- 14.31 --.
Column 11, line 40, "4triazol" should read -- 4-triazol --.
Column 12, line 56, "ml.0." should read -- ml.). --.
Column 13, line 11, "251°-253°" should read -- 251-253.5° --.
Column 13, line 22, "105°-137°" should read -- 105-137.5° --.
Column 13, line 23, "4chloro..." should read -- 4-chloro... --.
Column 13, line 27, "3-hydroxy..." should read -- 3-(hydroxy... --.
Column 13, line 30, "1,2,3-" should read -- 1,2,4- --.
Column 13, line 42, "5-4H-" should read -- 5-methyl-4H- --.
Column 15, line 39, "3-hydroxy..." should read -- 3-(hydroxy... --.

Signed and Sealed this

Twelfth Day of May 1981

[SEAL]

Attest:

RENE D. TEGTMEYER

Attesting Officer     Acting Commissioner of Patents and Trademarks